United States Patent [19]

DeMarinis

[11] Patent Number: 4,469,634

[45] Date of Patent: Sep. 4, 1984

[54] ALLYLOXY- AND ALLYLTHIO-2,3,4,5-TETRAHYDRO-1H-3-BENZAZEPINES

[75] Inventor: Robert M. DeMarinis, Ardmore, Pa.

[73] Assignee: SmithKline Beckman Corporation, Philadelphia, Pa.

[21] Appl. No.: 403,229

[22] Filed: Jul. 29, 1982

[51] Int. Cl.³ .......................................... C07D 223/16
[52] U.S. Cl. .............................................. 260/239 BB
[58] Field of Search ................. 260/239 BB; 546/150

[56] References Cited

U.S. PATENT DOCUMENTS 3,963,725  6/1976  Kishimoto et al. ................ 546/150
4,210,749  7/1980  Shetty ......................... 260/239 BB
4,233,217  11/1980 Shetty ......................... 260/239 BB

*Primary Examiner*—Richard Raymond
*Assistant Examiner*—D. B. Springer
*Attorney, Agent, or Firm*—William H. Edgerton; Richard D. Foggio; Alan D. Lourie

[57] ABSTRACT

A series of allyloxy- and allylthio-2,3,4,5-tetrahydro-1H-3-benzazepines has been prepared and found to have utility as $\alpha_2$-antagonists and as intermediates for preparing $\alpha_2$-adrenergic affinity resins.

7 Claims, No Drawings

ALLYLOXY- AND ALLYLTHIO-2,3,4,5-TETRAHYDRO-1H-3-BENZAZEPINES

This invention comprises a series of compounds whose structures are characterized by a 2,3,4,5-tetrahydro-1H-3-benzazepine nucleus which is substituted by either an allyloxy- or allylthio- group in the benz- ring. The compounds have alpha$_2$-antagonist activity and are useful, also, in preparing affinity chromatographic resins when attached to an agarose bead gel by means of a hydrophilic spacer moiety.

The compounds of this invention are exemplified by the structural formula:

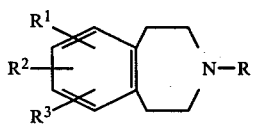

in which:

R is hydrogen or lower alkyl of 1-6 carbons; and,
R$^1$, R$^2$ and R$^3$ are allyloxy, allylthio, halo such as fluoro, chloro or bromo or hydrogen, provided that one of R$^1$, R$^2$ and R$^3$ must be allyloxy or allylthio.

More specifically, a subgeneric group of compounds is represented by the structural formula:

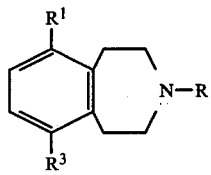

in which R, R$^1$ and R$^3$ are as described above provided that one of R$^1$ and R$^3$ is allyloxy.

An advantageous group of compounds is represented by formula I in which either R$^1$ or R$^3$ is allyloxy. A species of particular utility is 6-allyloxy-9-chloro-3-methyl-2,3,4,5-tetrahydro-1H-3-benzazepine or one of its acid addition salts.

Also included in this invention are the pharmaceutically acceptable, acid addition salts of the abovedescribed compounds with nontoxic acids, such as hydrochloric, sulfuric, sulfamic, acetic, propionic, nitric, hydrobromic, hydriodic, maleic, malic, methane sulfonic, ethanedisulfonic, p-toluenesulfonic or phosphoric acid salts. The salts are prepared by reacting the bases of this invention in an organic solvent with an excess of the chosen acid.

The compounds of this invention have anti-hypertensive activity with their mechanism of action being adrenergic alpha$_2$-antagonism.

This activity is demonstrated in vitro by determining the prejunctional alpha$_2$-antagonist activity using the isolated superfused guinea pig left atrium. Briefly, the heart is removed from a pentobarbital-anesthetized male guinea pig. The left atrium is removed, dissected free of extraneous tissue and mounted in a 2 ml superfusion chamber. The tissue is paced at 60 pulse/minute and the sympathetic nerves excited at 6 minute intervals by field stimulation. The response to nerve stimulation is measured as the difference in contractile force between the basal contraction and peak contraction following a nerve stimulation. A concentration-response curve for clonidine (a known alpha$_2$-agonist) is prepared by administering increasing concentrations of clonidine following each successive stimulation. The tissue is, then, superfused with the alpha$_2$-antagonist to be tested for thirty minutes and the clonidine concentration-effect curve is repeated in the presence of antagonist. The receptor dissociation constant of the antagonist ($K_B$) is defined as the antagonist concentration required to shift the log concentration-response curve of the agonist to the right by a factor of 2.

Selectivity for the alpha$_2$ vis-a-vis the alpha$_1$-adrenoceptor is determined by comparing the $K_B$, obtained as described above, with the $K_B$ on the alpha$_1$ receptor determined in the rabbit ear artery segment as an antagonist of the constrictor response which is induced by norepinephrine.

Details of the test system used to demonstrate alpha$_2$-antagonist activity, as well as activity of the standard antihypertensive compound, clonidine, are given in J. P. Hieble and R. G. Pendleton, Arch. Pharmacol. 309 217-224 (1979).

The compounds of formula I also have utility for preparing affinity resins for chromatographic separation, or concentration, of alpha$_2$-adrenergic receptor containing material from human platelets. Affinity chromatography is used in biological research for isolating or purifying biologically active materials, see M. G. Caron et al., J. Biol. Chem. 254 2923 (1979) for a description of a similar procedure for concentrating β-adrenergic receptors containing matter derived from frog erythrocytes. The affinity adsorbent using the compounds of this invention is prepared using a compound of formula I, especially 6-allyloxy-9-chloro-3-methyl-2,3,4,5-tetrahydro-1H-3-benzazepine, attached to a modified agarose column by a spacer derived from 1,4-butanediol diglycidyl ether. The benz- allyl substituent in the structures of the compounds of this invention is necessary for binding to the supporting agarose resin.

The compounds of formula I are prepared by reacting an allyl halide, such as allyl chloride or bromide, with a hydroxy or mercapto-2,3,4,5-tetrahydro-1H-3-benzazepine which is optionally substituted at the N-position by either a lower alkyl or a blocking acyl group, such as a lower alkanoyl or lower alkyl carbonate. The reaction is carried out in the presence of an acid binding agent such as sodium methoxide, sodamide, sodium hydride, potassium hydride, potassium carbonate, sodium hydroxide or potassium hydroxide. A solvent, usually an organic one in which the reactants are soluble such as dimethylformamide, dimethyl acetamide, a lower alcohol or dimethylsulfoxide, is commonly used. The reaction is run with a temperature chosen from the range of about 0° up to the reflux point of the reaction mixture until the reaction is complete. If a N-blocking group is used, it is either removed by standard chemical reactions or reduced to the corresponding N-lower alkyl by a reducing agent which is commonly used for converting acylamino groups to alkylamino groups, such as lithium aluminum hydride. The desired end products are isolated by conventional chemical methods, either as the free bases or their pharmaceutically acceptable acid addition salts.

The following examples are to illustrate the preparation and use of the compounds of this invention. All temperatures are in degrees Centigrade.

EXAMPLE 1

A solution of 4.02 g [0.018 mol, B. Pecherer et. al., J. Het. Chem. 8, 779 (1971)] of 3-acetyl-7-chloro-2,3,4,5-tetrahydro-1H-3-benzazepine and 3.78 g (0.054 mol) of sodium thiomethoxide in 37.5 ml of hexamethylphosphorus triamide was heated to 125° for 4 hours. The mixture was cooled in an ice bath and treated with 4.36 g (0.036 mol) of allyl bromide. The mixture was allowed to warm to room temperature and stirred overnight. It was poured into 375 ml of saturated sodium chloride and extracted with ether. The combined ether extracts were washed with water (3×100 ml), dried over anhydrous sodium sulfate and concentrated. The residue was chromatographed over silica gel, eluting with ethyl acetate, to give a solid which was recrystallized from cyclohexane to give off-white crystals; m.p. 73°-74°. This was dissolved in ethanol and aqueous 20% sodium hydroxide and heated at reflux for 24 hours. The solution was poured into ice-water and extracted with methylene chloride. The methylene chloride was dried and evaporated to leave a residue which was taken up in ether and precipitated by the addition of ethereal hydrogen chloride. The resulting salt was removed by filtration and, then, recrystallized from isopropanol to give white crystals of 7-allylthio-2,3,4,5-tetrahydro-1H-3-benzazepine hydrochloride; m.p. 150°-151°.

Anal. Calc'd for $C_{13}H_{17}NS.HCl.0.2H_2O$: C, 60.19; H, 7.15; N, 5.40. Found: C, 60.33; H, 7.04; N, 5.51.

Biological activity: $K_B$, guinea pig atrium, 380 nM.

EXAMPLE 2

To a cold solution of 67.2 g (0.34 mol, U.S. Pat. No. 4,265,890) of 6-chloro-3-methyl-2,3,4,5-tetrahydro-1H-3-benzazepine in 100 ml of sulfuric acid was added, dropwise over 2 hours, 40 ml of concentrated nitric acid. The mixture was stirred at room temperature overnight and quenched in ice. It was made basic with 10% sodium hydroxide solution and extracted with methylene chloride. The organic phase was washed, dried and evaporated to leave a residue, which was chromatographed over a "Waters prep 500" high pressure liquid chromatographic silica gel column, using isopropanol-hexane-diethylamine, to give pure 6-chloro-3-methyl-9-nitro-2,3,4,5-tetrahydro-1H-3-benzazepine.

A solution of 10 g (0.04 mol) of the nitro compound and 6.0 ml of hydrazine hydrate in 400 ml of ethanol was warmed to 45° while activated Raney nickel was added in small portions until the evolution of gas ceased. The mixture was cooled, filtered through a filter aid and concentrated to give 9-amino-6-chloro-3-methyl-2,3,4,5-tetrahydro-1H-3-benzazepine.

This compound was dissolved in 85 ml of 3N sulfuric acid and cooled in an ice bath while a solution of 3.72 g (54 mmol) of sodium nitrite in 18.5 ml of water was added dropwise. After the addition had been completed, the solution was stirred for 10 minutes, then, added dropwise to 500 ml of 50% sulfuric acid maintained at 80° and stirred for an additional hour after completion of addition. The solution was cooled in the freezer at −20°. Crystals formed, which were removed by filtration. These were dissolved in water, neutralized to pH 8.0 with ammonium hydroxide and extracted with methylene chloride. The organic phase was dried and evaporated to give 6-chloro-9-hydroxy-3-methyl-2,3,4,5-tetrahydro-1H-3-benzazepine, as a crystalline solid, m.p. 178°-180°.

A solution of 2.12 g (10 mmol) of this compound in 25 ml of dry dimethylformamide was cooled in an ice bath while 0.48 g (10 mmol) of 50% sodium hydride was added. This was stirred till complete solution was effected and the solution treated with 1.01 g (10 mmol) of allyl bromide in 10 ml of dry dimethylformamide. It was stirred at room temperature for 20 hours, quenched in water and extracted with methylene chloride. The organic extracts were washed with water, dried and evaporated to a solid residue of the desired base which was taken up in ether and precipitated with ethereal hydrogen chloride. The precipitated solid was collected and recrystallized from methanol-ether to give off-white crystals of 9-allyloxy-6-chloro-3-methyl-2,3,4,5-tetrahydro-1H-3-benzazepine hydrochloride, m.p. 197°-199°.

Anal. Calc'd for $C_{14}H_{18}ClNO.HCl$: C, 58.34; H, 6.64; N, 4.86. Found: C, 58.40; H, 6.62; N, 4.86.

Biological activity: $K_B$, guinea pig atrium, 320 nM, $EC_{50}$, platelet, 90 nM.

Substituting a stoichiometric quantity of 6-fluoro-3-methyl-2,3,4,5-tetrahydro-1H-3-benzazepine or 6-bromo-3-methyl-2,3,4,5-tetrahydro-1H-3-benzazepine for the 6-chloro congener in the above sequence of reactions gives 9-allyloxy-6-fluoro-3-methyl-2,3,4,5-tetrahydro-1H-3-benzazepine and its hydrochloride salt or 9-allyloxy-6-bromo-3-methyl-2,3,4,5-tetrahydro-1H-3-benzazepine and its hydrochloride salt.

EXAMPLE 3

A mixture of 0.95 g (4.6 mmmol) of 3-acetyl-7-hydroxy-2,3,4,5-tetrahydro-1H-3-benzazepine, 0.75 g (5.5 mmol) of anhydrous potassium carbonate and 0.66 g (5.4 mmol) of allyl bromide in 50 ml of dry acetone was stirred and heated at reflux for 7 hours. The acetone was removed under vacuum and the residue partitioned between water and methylene chloride. The organic phase was washed with water, dried and evaporated to give a solid which was dissolved in 14 ml of ethanol and treated with 3 g of sodium hydroxide in 14 ml of water. The solution was heated at reflux for 15 hours, poured into ice-water and extracted with methylene chloride. The organic layer was washed with water, dried and evaporated. The residual base was taken up in a small amount of isopropanol and precipitated with ethereal hydrogen chloride. The resulting solid could be crystallized from acetone to give a white solid; 7-allyloxy-2,3,4,5-tetrahydro-1H-3-benzazepine hydrochloride, m.p. 153°-154°.

Anal. Calc'd for $C_{13}H_{17}NO.HCl$: C, 64.16; H, 7.62; N, 5.76. Found: C, 64.24; H, 7.01; N, 5.88.

EXAMPLE 4

Into 10 ml of hexamethylphosphorus triamide was dissolved 784 mg (4 mmol) of 6-chloro-2,3,4,5-tetrahydro-3-methyl-1H-3-benzazepine and 840 mg (12 mmol) of sodium thiomethoxide. The reaction was heated to 125° for 4 hours, cooled to ice-bath temperature and 968 mg (18 mmol) of allyl bromide was added in one portion. The mixture was warmed to room temperature and stirred overnight. It was poured into 75 ml of brine and extracted with three 75 ml portions of ether. The combined extracts were washed with three 50 ml portions of water, dried over magnesium sulfate and treated with excess ethereal hydrogen chloride. The solvent was reduced to 10 ml and decanted from an insoluble oil. The oil was triturated with 10 ml ether which was removed and discarded. The residue was taken up in hot ethanol, diluted with ether and allowed to crystallize. The precipitate was removed and recrystallized from acetonitrile to give 6-allylthio-3-methyl-2,3,4,5-tetrahydro-1H-3-benzazepine hydrochloride, as white crystals, m.p. 158°–160°.

Anal. Calc'd for $C_{14}H_{19}NS.HCl$: C, 62.32; H, 7.47; N, 5.19. Found: C, 62.48; H, 7.47; N, 5.14.

EXAMPLE 5

A solution of 3-methoxyphthalic acid (19.6 g, 0.1 mol) in 100 ml of tetrahydrofuran was added to 10 g (0.263 mol) of lithium aluminum hydride in 500 ml of anhydrous ether at a rate sufficient to maintain a constant reflux. The mixture was refluxed for 2 hours after the addition was completed. It was cooled and decomposed by the addition of 10 ml of water, 20 ml of 10% sodium hydroxide and 40 ml of water. The resulting solid was separated by filtration and washed with tetrahydrofuran. The combined filtrates were concentrated to give 12 g of 3-methoxy-o-xylene-$\alpha,\alpha'$-diol; m.p. 95°.

To a solution of 1.68 g (0.01 mol) of the diol in 4.7 ml (0.06 mol) of pyridine and 10 ml of toluene, was added dropwise 4.37 ml (0.06 mol) of thionyl chloride. The mixture was stirred at room temperature for 2 hours. Water (50 ml) was added and the organic layer separated, washed with 3N hydrochloric acid, 10% sodium hydroxide and water. The organic layer was dried, filtered and evaporated to give 1.8 g of an oil, 3-methoxy-1,2-bis-benzyl chloride.

A solution of 60 g (0.292 mol) of the dichloro compound in 600 ml of dimethylsulfoxide was stirred while finely powdered sodium cyanide (57.36 g; 1.19 mol) was added, keeping temperature below 50°. The mixture was stirred at 40°–45° for 4 hours, cooled and diluted with 2 l of ice water to give a white solid. It was separated, washed with water and dried to give 42 g of white solid; 3-methoxy-o-phenylenediacetonitrile, m.p. 103°.

Twenty grams (0.107 mol) of dinitrile was cyclized using the procedure of Ruggli et. al., Helv. Chim. Acta. 18, 1338 (1935), to obtain 15 g of 6-methoxy-2,3,4,5-tetrahydro-1H-3-benzazepine as an oil.

The 6-methoxy-2,3,4,5-tetrahydro-1H-3-benzazepine (1.00 g; 0.0056 mol) was heated at reflux in 15 ml of 48% hydrobromic acid, overnight, under argon. It was concentrated to obtain a brown solid which was dispersed in acetonitrile; the mixture was filtered and the solid dried to give 0.94 g of 6-hydroxy-2,3,4,5-tetrahydro-1H-3-benzazepine hydrobromide, m.p. 220°–224°.

To a solution of 0.9 g (0.0036 mol) of the 6-hydroxy compound in 3 ml of pyridine was added 5 ml of ethyl chloroformate, while cooling. It was allowed to stir at room temperature for an hour, then, poured over 20 ml of 3N hydrochloric acid in ice and extracted with methylene chloride. The organic layer was washed with 10% sodium hydroxide, 3N hydrochloric acid and water, dried and evaporated to give 0.7 g of bis-carbethoxy compound. This was dissolved in 10 ml of ethanol and 10 ml of 10% sodium hydroxide solution was added. The mixture was heated to 50° for 30 minutes, cooled, diluted with water, made acidic and extracted with methylene chloride. The extracts were dried and evaporated to give 0.4 g of 6-hydroxy-3-carboethoxy-2,3,4,5-tetrahydro-1H-3-benzazepine.

A mixture of 0.4 g (0.0017 mol) of the phenol, 0.242 g (0.002 mol) of allyl bromide and 0.276 g (0.002 mol) of anhydrous potassium carbonate in 20 ml of dry acetone was heated at reflux for 8 hours. It was diluted with water, extracted with methylene chloride, washed twice with 10% sodium hydroxide and dried. After filtration, removal of the solvent gave 0.4 g of 6-allyloxy-3-carbethoxy-2,3,4,5-tetrahydro-1H-3-benzazepine.

To a solution of 0.4 g (0.0015 mol) of the carbamate in 50 ml ether under argon was added 0.735 (0.019 mol) of lithium aluminum hydride. The mixture was refluxed for 5 hours, cooled, and decomposed with water-alkali. The solid was removed by filtration and concentrated. Addition of ethereal hydrogen chloride gave a solid which was recrystallized from acetone/ether to give 0.158 g of 6-allyloxy-3-methyl-2,3,4,5-tetrahydro-1H-3-benzazepine hydrochloride.

Anal. Calc'd for $C_{14}H_{19}NO.HCl.\frac{1}{4}H_2O$: C, 65.11; H, 8.00; N, 5.42. Found: C, 65.26; H, 8.15; N, 5.34.

Biological activity: $K_B$, guinea pig atrium, 160 nM.

The same general procedure is used with propionyl chloride instead of ethyl chloroformate to give 6-allyloxy-3-propyl-2,3,4,5-tetrahydro-1H-3-benzazepine hydrochloride.

EXAMPLE 5

Preparation of the Affinity Adsorbent

The Sepharose* CL-4B affinity gel with the product of Example 2 was prepared with minor modifications according to the method described by Caron et. al., (loc. cit.) for the synthesis of Sepharose* 4B-alprenolol. One end of the bisoxirane, 1,4-butanediol diglycidylether, was attached under basic conditions to Sepharose* CL-4B. This is a modified agarose bead gel marketed by Pharmacia and described by Caron et al., (loc. cit.) and U.S. Pat. No. 4,237,267. Agarose is a purified linear galactan hydrocolloid isolated from agar marine algae.

The unreacted epoxide terminus was treated with sodium thiosulfate and reduced with dithioerythritol to form a free sulfhydryl. The allyloxy substituent of the benzazepine was, then, coupled to the sulfhydryl group via a free radical reaction.

This reaction was performed as follows: To 6 g of moist gel was added 100 mg of the benzazepine (as the hydrochloride salt) in 3 ml of water. The slurry was placed in a water bath at 70° and 100 $\mu$l of 0.17M potassium persulfate was added every 12 minutes for two hours. Following the coupling reaction, the gel was treated with sodium borohydride to return any oxidized sulfhydryl residues to the reduced state. The washed gel was, then, suspended for 2 hours at room temperature in 10 ml of 0.2M sodium bicarbonate containing 100 mmol iodoacetamide to alkylate free sulfhydryl groups. Finally, the gel was exhaustively washed with 1M sodium chloride solution and distilled water.

The concentration of the allyloxybenzazepine coupled to the Sepharose CL-B resin was estimated by both difference analysis of unreacted material and by direct ultraviolet spectroscopy of the gel in ethylene glycol.

What is claimed is:

1. A compound of the structural formula:

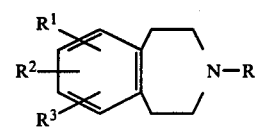

in which:

R is hydrogen or a lower alkyl of 1–6 carbons; and $R^1$, $R^2$ and $R^3$ are allyloxy, allylthio, halo or hydrogen, with the proviso that one of $R^1$, $R^2$ and $R^3$ is allyloxy or allylthio; or a pharmaceutically acceptable acid addition salt thereof.

2. The compound of claim 1 in which the benzallyloxy or allylthio substituent is substituted at a position alpha to the azepine ring.

3. The compound of claim 1 being 9-allyloxy-6-chloro-3-methyl-2,3,4,5-tetrahydro-1H-3-benzazepine or a pharmaceutically acceptable, acid addition salt thereof.

4. The compound of claim 1 being 9-allyloxy-6-chloro-3-methyl-2,3,4,5-tetrahydro-1H-3-benzazepine hydrochloride.

5. The compound of claim 1 being 7-allylthio-2,3,4,5-tetrahydro-1H-3-benzazepine.

6. The compound of claim 1 being 6-allyloxy-3-methyl-2,3,4,5-tetrahydro-1H-3-benzazepine.

7. The compound of claim 1 being 7-allyloxy-2,3,4,5-tetrahydro-1H-3-benzazepine.

* * * * *